United States Patent [19]

Dean et al.

[11] 4,419,450
[45] Dec. 6, 1983

[54] PLASMID CLONING VECTOR FOR BACILLUS SUBTILIS

[75] Inventors: Donald H. Dean, Worthington; Margaret M. Dooley, Columbus, both of Ohio

[73] Assignee: CPC International Inc., Englewood Cliffs, N.J.

[21] Appl. No.: 370,431

[22] Filed: Apr. 21, 1982

[51] Int. Cl.³ .................. C12N 1/20; C12N 1/00; C12N 15/00
[52] U.S. Cl. .................. 435/253; 435/317; 435/172
[58] Field of Search .............. 435/172, 317, 253

[56] References Cited

PUBLICATIONS

Lofdahl, et al., Gene, 3, 161–172, (1978).
Gryczan, et al., J. Bacteriology, 141, 246–253, (1980).
Weisblum, et al., J. Bacteriology, 137, 635–643, (1979).
Polak, et al., Plasmid, 7, 152–162, (1982).
Kreft, et al., Molec. Gen. Genet., 162, 59–67, (1978).
Keggins, et al., Proc. Natl. Acad. Sci., U.S.A., 75, 1423–1427, (1978).
Gryczan, et al., Proc. Natl. Acad. Sci., U.S.A., 75, 1428–1432, (1978).

*Primary Examiner*—Alvin E. Tanenholtz
*Attorney, Agent, or Firm*—Stanley M. Parmerter

[57] ABSTRACT

A novel chemical compound, plasmid pOS4, is prepared by joining fragments of the plasmids pSE3 and pE194. The pOS4 plasmid, containing kanamycin resistance and erythromycin resistance coding genes, is useful as a cloning vehicle in recombinant DNA work.

2 Claims, 1 Drawing Figure

PLASMID CLONING VECTOR FOR *BACILLUS SUBTILIS*

FIELD OF THE INVENTION

This invention relates to a new synthetic plasmid, pOS4, useful as a cloning vehicle into which various genes can be inserted using recombinant DNA methodology.

BACKGROUND OF THE INVENTION

Most genetic material in a bacterium exists as giant DNA molecules which are present as the chromosome of the cell. However, a certain amount of the genetic material may also be present in the form of smaller closed circular molecules of DNA, known as plasmids.

The portion of the DNA molecule related to a specific hereditary trait is called a gene. By techniques referred to as genetic engineering, it is possible to transfer a gene, which codes for the production of a specific protein, from one microorganism to another. Various workers have used these techniques to develop microorganisms which are superior producers of certain proteins such as enzymes.

It has been discovered that plasmids, which contain a series of genes linked together in the form of a circle, can be removed from the cells of one microorganism and inserted into the cells of another microorganism with comparative ease. Plasmids can also be used as vectors to carry new genetic material into a host organism. This is accomplished by first cutting the plasmid with an enzyme, known as a restriction endonuclease, that opens the circle of DNA. A fragment of foreign DNA, containing the desired gene, is inserted into the place where the DNA circle was cut. The circle is reformed by treatment with another enzyme known as a DNA ligase. The recombined plasmid, a new circular DNA molecule, contains the genes of the original plasmid plus the new gene from the piece of DNA which was inserted. This plasmid can be introduced into a host microorganism. The plasmid containing the new gene is then reproduced in the host microorganism and becomes part of its genetic material. The microorganism containing the recombined plasmid then produces the proteins coded for by the genes of this plasmid.

One microorganism that is easily grown on a commercial scale is *Bacillus subtilis*, hereafter abbreviated *B. subtilis*. For this reason, researchers have sought to find plasmid vectors which can be inserted into *B. subtilis* and which will multiply in that host. It is important that the plasmid vector contain some markers which permit easy identification of the presence of that plasmid in the host. Furthermore, it should be possible to insert DNA fragments into the vector without altering its ability to replicate in the *B. subtilis*.

Several workers have described either naturally-occurring or synthetic plasmids which replicate in *B. subtilis*. These include Kreft, et al, Molec. Gen. Genet., 162, 59–67 (1978); Keggins, et al, Proc. Natl. Acad. Sci., U.S.A., 75, 1423–1427 (1978); Gryczan, et al, Proc. Natl. Acad. Sci., U.S.A., 75, 1428–1432 (1978); and Gryczan, et al, J. Bacteriology, 141, 246–253 (1980). The plasmid vectors disclosed by these workers contain antibiotic resistance markers to permit their identification in a host.

The present invention is directed to a new synthetic plasmid vector having two antibiotic resistance markers. This vector can be combined with genetic material to form hybrid plasmids that are readily inserted into and maintained in the industrially important microorganisms of the species *B. subtilis*.

SUMMARY OF THE INVENTION

In accordance with this invention, there is provided an essentially pure plasmid, pOS4, having erythromycin resistance and kanamycin resistance coding genes characterized by a molecular weight of approximately 5.8 kilobases (kb) and a restriction endonuclease cleavage map as shown in the drawing.

In addition, there is provided a biologically pure culture of *B. subtilis*, ATCC 39,097, characterized in that its cells contain the plasmid, pOS4, and that it will grow on a medium containing 5 $\mu$g of kanamycin and 5 $\mu$g of erythromycin per ml of medium.

DESCRIPTION OF THE DRAWING

The drawing depicts the restriction endonuclease cleavage map for pOS4. The map is constructed on the basis of plasmid pOS4 having a molecular weight of about 5.8 kb. The map positions of the various restriction sites are given as kilobase coordinates relative to the Bam HI restriction site at 0.0/5.8 kb. The restriction endonuclease abbreviations are as follows:

(1) Bam HI is an enzyme from *Bacillus amyloliquefaciens H*;
(2) Bcl I is an enzyme from *Bacillus caldolyticus*;
(3) Bgl II is an enzyme from *Bacillus globigii*;
(4) Eco RI is an enzyme from *Escherichia coli*;
(5) Hae III is an enzyme from *Haemophilus aegyptius*;
(6) Hpa I is an enzyme from *Haemophilus parainfluenzae*;
(7) Xba I is an enzyme from *Xanthomonas badrii*.

DETAILED DESCRIPTION OF THE INVENTION

Figure 1:
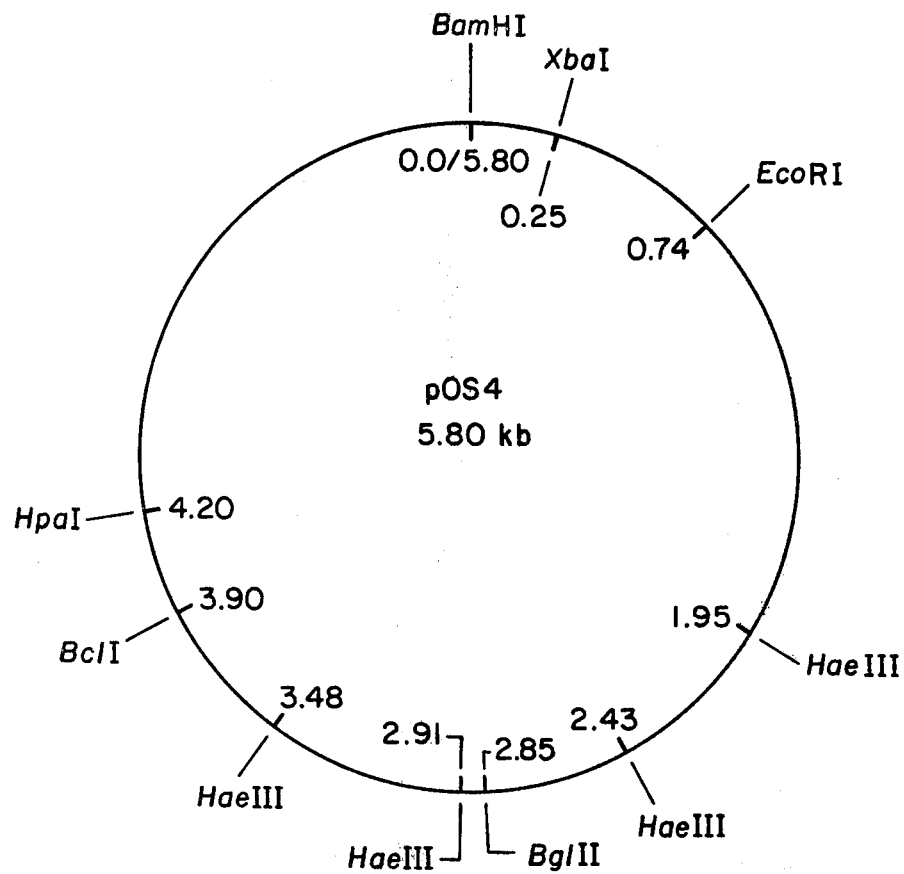

Plasmid pOS4 was constructed from DNA fragments of two previously known plasmids, pSE3 and pE194-cop6. Plasmid pSE3, originally isolated from *Staphylococcus epidermidus*, carries a kanamycin resistance gene and has a temperature-resistant origin of replication. It has a molecular weight of 4.5 kb. This plasmid has been inserted into *B. subtilis* and a strain of *B. subtilis* carrying this plasmid is available from the American Type Culture Collection as ATCC 39,098.

Plasmid pE194-cop6 was described by Weisblum, et al, J. Bacteriology, 137, 635–643 (1979). It has a molecular weight of 3.6 kb and contains an erythromycin resistance gene. It also has a temperature sensitive origin of replication and will not replicate optimally at temperatures above about 32° C. A strain of *B. subtilis* containing this plasmid is available from the American Type Culture Collection as ATCC 39,089.

Plasmids pSE3 and pE194-cop6 were cut by the restriction endonuclease Hpa II, an enzyme from *Haemophilus parainfluenzae*. This endonuclease did not destroy the antibiotic resistance markers of the plasmids. The resulting mixture of linear DNA sequences was treated with a ligase using techniques well known in the art. The ligase used for this purpose was the commercially available T$_4$ DNA ligase.

The plasmids obtained from the ligation reaction were made biologically active by transforming them into host cells of a strain of *B. subtilis* RM125. This strain, which shows neither kanamycin nor erythromycin resistance, was originally described by Uozumi, et al, Molec. Gen. Genet., 152, 65–69 (1977). It is available as ATCC 39,088. Transformation was accomplished by the protoplast transformation method of Chang and Cohen, Molec. Gen. Genet., 118, 111–115 (1979).

Cells were obtained which grew in the presence of erythromycin and kanamycin at 45° C. These cells contained a plasmid with a temperature-resistant replication mechanism as well as with the two antibiotic resistance markers.

The synthetic plasmid produced by the host cells was isolated using a modification of the cleared lysate procedure of Birnboim and Doly, Nuc. Acid Res., 7, 1513–1523 (1979). The plasmid was purified by CsCl-ethidium bromide density gradient ultracentifugation.

Plasmid pOS4 obtained by this process is useful as a plasmid vector for making new recombinant plasmids which can be introduced into host bacteria by transformation. When the plasmid is used for this purpose, it is cut at a specific site by means of a restriction endonuclease. The plasmid, which is a circular DNA molecule, is thus converted into a linear DNA molecule by the enzyme which cuts the DNA. Other DNA containing a gene coding for a desired protein is similarly cleaved with the same enzyme. Upon mixing the linear vector, or portions thereof, and nonvector DNA containing the desired gene, their single-stranded or blunt ends can pair with each other and, in the presence of a ligase, can be covalently joined to form a single circle of DNA.

For example, this procedure can be used to insert a length of DNA which codes for an amylase enzyme into the cut pOS4 plasmid. The resulting circular DNA molecules consist of plasmid pOS4 with an inserted length of DNA coding for the synthesis of amylase. The new synthetic plasmid, containing the desired genetic material, can be introduced into a host microorganism for further replication with the resulting production of quantities of the desired amylase enzyme.

An important feature of plasmid pOS4 is that it has single recognition sites for six different restriction enzymes: Bam HI, Bcl I, Bgl II, Eco RI, Hpa I and Xba I. This permits insertion of DNA fragments that have been cut with these enzymes. When the plasmid is cut with Bgl II, the kanamycin resistance gene is destroyed. Cleavage of the plasmid with Bcl I or Hpa I, on the other hand, destroys the erythromycin resistance. Such insertional inactivation adds to the versatility of pOS4 as a vector since it permits easy isolation of cells containing recombinant plasmids with gene insertions at specific locations.

Plasmid pOS4 is particularly useful because it can function as a plasmid vector in microorganisms such as B. subtilis and certain other gram-positive hosts. When strains of B. subtilis are used as the host for the synthetic plasmids, the enzymes or other proteins produced by the cells can be exported from the cells into the medium. This is important for commercial production of the enzyme or other protein since an expensive cell lysing step is avoided. The B. subtilis is a particularly desirable host because it is a species readily adapted to large-scale industrial fermentations.

The following example illustrates certain embodiments of the present invention. Unless otherwise stated, all proportions and percentages are provided on the basis of weight.

All strains bearing ATCC numbers are available from the American Type Culture Collection, Rockville, Maryland. All reagents bearing the Difco name are available from the Difco Laboratories, Detroit, Mich.

EXAMPLE

Isolation of Plasmid pSE3

A culture of B. subtilis, ATCC 39,098, was grown in L-broth (1% Difco tryptone, 0.5% Difco yeast extract, 0.5% NaCl) in the presence of kanamycin at a concentration of 5 μg/ml. The cells were harvested by centrifugation and cleared lysates were then prepared from the cells by a modification of the method of Birnboim and Doly, Nuc. Acid Res., 7, 1513–1523 (1979). Solutions I, II, and III were prepared as specified in the published procedure. The cell pellet was resuspended in 20 ml of Solution I. After incubation at room temperature from 30 minutes to 1 hour, 40 ml of Solution II was added. The suspensions were mixed and held at 0° C. for 5 to 20 minutes before the addition of 30 ml of Solution III. Mixing was accomplished by gentle inversion and the lysates were stored at 0° C. for at least 1 hour. The resulting precipitate was collected by centrifugation at $10,000 \times g$ for 15 minutes. The supernatant was removed by decantation and again centrifuged to remove the remaining precipitate. The solution was mixed with a two-fold excess of cold ethanol at $-20°$ C. and stored at $-20°$ C. for at least 1 hour to precipitate the DNA. The resulting precipitate was collected by centrifugation and dissolved in 5–10 ml of 0.05 molar tris(hydroxymethyl)aminomethane hydrochloride (hereafter written Tris-HCl) at pH 8.0 containing 0.1 M sodium acetate. The alcohol precipitation was repeated except that this time a solution containing 0.015 M NaCl and 0.0015 sodium acetate at pH 7 was used to dissolve the precipitate. The lysate was then incubated at 37° C. for at least 30 minutes with a mixture of 0.1 mg/ml of Ribonuclease-A (Type 1-A from Bovine Pancreas, available from Sigma Chemical Company, St. Louis, Mo.) and 1 to 10 units/ml of Ribonuclease-T1 (Grade IV from Aspergillus oryzae, Sigma Chemical Company). The lysates were then extracted once with redistilled phenol which had been equilibrated with three changes of a two-fold excess of TES (TES is 30 mM Tris-HCl, pH 8.0, 50 mM NaCl, 5 mM ethylene-diaminetetraacetic acid). The phenol treatment was followed by one extraction with a 24 to 1 mixture of chloroform and isoamyl alcohol.

The cleared lysate was diluted to 8 ml with $10 \times$ TES and sufficient water to give a final concentration of approximately $1 \times$ TES. To this solution was added 8.0 g of CsCl and the intercalating dye, ethidium bromide, to a concentration of approximately 0.5 mg/ml. The plasmid DNA was separated from the total DNA by the general ultracentrifugation method of Radloff, et al, Proc. Natl. Acad, Sci., U.S.A., 57, 1514–1521 (1967). Plasmid pSE3, having a molecular weight of approximately 4.5 kb, was obtained.

Isolation of Plasmid pE194-cop6

A strain of B. subtilis carrying plasmid pE194-cop6, ATCC 39,089, was grown and the plasmid was isolated from the cells following the general procedure used for isolation of the plasmid pSE3. This plasmid has a molecular weight of approximately 3.6 kb. It is described by Weisblum, et al, J. Bacteriology, 137, 635–643 (1979).

Preparation of Plasmid pOS4

Purified plasmids pSE3 and pE194-cop6 were mixed and concentrated by a rapid alcohol precipitation procedure. A one-tenth volume of 3 M sodium acetate solution was added to the purified plasmid solution in a centrifuge tube. A two-fold excess of ethanol at −20° C. was added and the tube was kept at −80° C. for 25 minutes. The precipitate was collected by centrifugation and washed twice with 70% ethanol, dried under vacuum and redissolved in a buffer solution. The solution was then digested with an excess of Hpa II enzyme, available from the Bethesda Research Laboratories Inc., Gaithersburg, Md., using the buffer specified by this manufacturer. When the digestion was more than 95% complete as determined by agarose gel electrophoresis, the restriction enzyme was inactivated by heating at 65° C.

The solution of the cut plasmids was ligated at 0° C. for 48 hours using an excess of T4 DNA ligase (available from New England Biolabs Inc., Beverly, Mass.) using the buffer recommended by the supplier. A typical ligation mixture contained approximately equal quantities of digested pSE3 and pE194-cop6 at a DNA concentration of 260 µg/ml.

The ligated fragments of DNA obtained from the two donor plasmids were transformed into protoplasts of *B. subtilis*, ATCC 39,088. Transformation was accomplished by the protoplast transformation method of Chang and Cohen, Molec. Gen. Genet., 118, 111–115 (1979). The transformed protoplasts were incubated for at least 1 hour at 30° C. before the addition of erythromycin to a concentration of 0.05 µg/ml. After further incubation at 30° C. for at least 30 minutes, the protoplasts were plated on agar plates with DM3 medium containing 5 µg/ml of erythromycin. (DM3 consists of the following sterile solutions per liter: 200 ml 4% agar, 500 ml 1 M sodium succinate at pH 7.3, 100 ml 5% Difco casamino acids, 500 ml 10% Difco yeast extract, 100 ml 3.5% $K_2HPO_4$ and 1.5% $KH_2PO_4$, 25 ml 20% glucose, 20 ml 1 M $MgCl_2$, and 5 ml 2% Bovine serum albumin.) The plated cells were incubated at 30° C. Colonies grown on the DM3 plates containing erythromycin were patched in a grid pattern onto two TBAB (Tryptose Blood Agar Base) plates available from the Difco Laboratories, Detroit, Mich. These were incubated separately at 30° C. and 45° C. These templates were replicate plated onto TBAB plates containing 5 µg/ml kanamycin and 5 µg/ml erythromycin. These plates were incubated at the same temperatures as the templates. Colonies growing on TBAB with antibiotics at 45° C. were separated and plasmids were isolated from them using the procedure described for the isolation of pSE3. One plasmid which conferred the desired properties and had appropriate restriction patterns was chosen for further study and designated as pOS4. A strain of *B. subtilis* containing the plasmid pOS4 is available from the American Type Culture Collection, Rockville, Md. as ATCC 39,097.

Strains of *B. subtilis* carrying the plasmid pOS4 can be grown in a suitable medium such as L-broth which preferably contains 5 µg/ml each of erythromycin and kanamycin. Growth is carried out at 30° C. to 37° C. To facilitate subsequent lysis, the culture is harvested when the cell density is such that the absorbance at 660 nanometers is about 0.6 to 0.7. Plasmid DNA is isolated and purified by the method used for isolation of the plasmid pSE3.

Analysis of Plasmid pOS4

Plasmid pOS4 was analyzed by restriction analysis in order to construct the map shown in the FIGURE. All restriction enzymes used were purchased from Bethesda Research Laboratories Inc. and used according to the procedures of Jalanko, et al, Gene, 14, 325–328 (1981). The enzymes Hae III, Hpa II, Bcl I, and Hpa I were used in a low-salt buffer containing 10 mM Tris at pH 7.6, 10 mM NaCl, 10 mM $MgCl_2$ and 1 mM dithiothreitol. The enzymes Bam HI, Bgl II, Bcl I, Eco RI, and Xba I used a similar buffer in which the NaCl is at a concentration of 50 mM. When combinations of enzyme requiring low- and high-salt buffers were used, the enzyme requiring low-salt was used first at 37° C. for 2 hours, then inactivated at 65° C. for 15 minutes. Additional NaCl was then added to bring the salt concentration to that of the high-salt buffer and the second enzyme was added for a 2-hour incubation at 37° C. Typically, a pOS4 solution containing approximately 2 µg in 5 µl was digested with 5 units of a restriction enzyme in 50 µl final volume for 2 hours at 37° C.

The results of single-enzyme digestions are given in Table I and of double-enzyme digestions are given in Table II. By comparison of the single- and double-digest data, the map of pOS4 given in FIG. 1 was obtained.

TABLE I
FRAGMENTS PRODUCED FROM pOS4 IN DIGESTS WITH SINGLE-RESTRICTION ENDONUCLEASES[a]

| Enzymes | 1 | 2 | 3 | 4 | Total |
|---|---|---|---|---|---|
| Hpa I | 5700 | — | — | — | 5700 |
| Bcl I | 5700 | — | — | — | 5700 |
| Bam HI | 5700 | — | — | — | 5700 |
| Hpa II | 2800 | 1950 | 780 | 150[b] | 5680 |
| Hae III | 4200 | 570 | 480 (× 2) | — | 5730 |

[a]Fragment sizes (and totals) are given as base pairs and are accurate within 5%.
[b]Observed only on polyacrylamide gels.

TABLE II
FRAGMENTS PRODUCED FROM pOS4 IN DIGESTS WITH DOUBLE-RESTRICTION ENDONUCLEASES[a]

| Enzymes | 1 | 2 | 3 | 4 | Total |
|---|---|---|---|---|---|
| Bgl II-Eco RI | 3645 | 2115 | — | — | 5760 |
| Bgl II-Bam HI | 2850 | 2850 | — | — | 5700 |
| Bgl II-Bcl I | 4700 | 950 | — | — | 5650 |
| Bgl II-Xba I | 3150 | 2600 | — | — | 5750 |
| Bcl I-Bam HI | 3900 | 1940 | — | — | 5840 |
| Bcl I-Xba I | 3570 | 2180 | — | — | 5750 |
| Hpa I-Bam HI | 4200 | 1380 | — | — | 5580 |
| Hae III-Bam HI | 2200 | 1950 | 570 | 480 (× 2) | 5680 |
| Hae III-Eco RI | 2820 | 1320 | 570 | 480 (× 2) | 5670 |

[a]Fragment sizes (and totals) are given as base pairs and are accurate within 5%.

Stability of the pOS4 plasmid in a host strain of *B. subtilis* was measured by the following experiment. Plasmid-bearing cells of B. subtilis Strain ATCC 39,097 were grown at 45° C. for 14 generations in a medium containing Difco Heart Infusion Broth. Cells were plated on Difco Tryptose Blood Agar Base plates. Clearly separated colonies from each dilution were picked onto antibiotic plates containing both erythromycin and kanamycin. After 14 generations, all of the cells showed reistance to both antibiotics indicating that no plasmid loss had occurred for 14 generations. This experiment indicates that the vector of this invention is stably maintained in a *B subtilis* host.

The work described herein was all done in conformity with physical and biological containment requirements specified in the NIH guidelines.

What is claimed is:

1. Essentially pure plasmid, pOS4, having erythromycin resistance and kanamycin resistance coding genes characterized by a molecular weight of approximately 5.8 kb and a restriction endonuclease cleavage map as shown in the drawing.

2. A biologically pure culture of *B. subtilis*, ATCC 39,097, characterized in that its cells contain the plasmid, pOS4, and that it will grow on a medium containing 5 µg of kanamycin and 5 µg of erythromycin per ml of medium.

* * * * *